United States Patent
Wee

(10) Patent No.: US 10,076,175 B2
(45) Date of Patent: Sep. 18, 2018

(54) DEVICE FOR STORING, MIXING, AND APPLYING COSMETIC, SKINCARE, FOOD, OR PHARMACEUTICAL PRODUCTS

(71) Applicant: Jonathan Eng Jin Wee, Tanjung Tokong (MY)

(72) Inventor: Jonathan Eng Jin Wee, Tanjung Tokong (MY)

(*) Notice: Subject to any disclaimer, the term of this patent is extended or adjusted under 35 U.S.C. 154(b) by 128 days.

(21) Appl. No.: 15/076,606

(22) Filed: Mar. 21, 2016

(65) Prior Publication Data

US 2016/0270511 A1  Sep. 22, 2016

Related U.S. Application Data

(60) Provisional application No. 62/135,295, filed on Mar. 19, 2015.

(51) Int. Cl.
| | |
|---|---|
| *A45D 40/24* | (2006.01) |
| *B65D 83/00* | (2006.01) |
| *A61M 35/00* | (2006.01) |
| *A45D 34/04* | (2006.01) |

(52) U.S. Cl.
CPC ............ *A45D 40/24* (2013.01); *A45D 34/04* (2013.01); *A61M 35/003* (2013.01); *B65D 83/0005* (2013.01)

(58) Field of Classification Search
CPC .... A45D 40/24; A45D 34/04; B65D 83/0005; B65D 83/0022; A61M 35/003
See application file for complete search history.

(56) References Cited

U.S. PATENT DOCUMENTS

| | | | | |
|---|---|---|---|---|
| 7,445,372 | B1* | 11/2008 | Engel | B01F 7/00758 222/145.6 |
| 2010/0185322 | A1* | 7/2010 | Bylsma | A61M 5/1413 700/239 |
| 2013/0264358 | A1* | 10/2013 | Fallat, II | A45D 34/04 222/136 |
| 2013/0277393 | A1* | 10/2013 | Rahm | B05C 17/00503 222/137 |
| 2016/0058156 | A1* | 3/2016 | Chiasson | A45D 40/24 132/200 |
| 2017/0340087 | A1* | 11/2017 | Samain | A45D 40/0075 |
| 2017/0367462 | A1* | 12/2017 | Samain | A45D 40/24 |
| 2017/0369229 | A1* | 12/2017 | Samain | B65D 83/682 |

* cited by examiner

*Primary Examiner* — J. Casimer Jacyna

(57) ABSTRACT

A device for storing, mixing and applying skincare, cosmetic, food and pharmaceutical products includes a tubular housing which is used to hold a plurality of dispensing canisters, a plurality of plungers, and a dispensing actuation hub. The plurality of dispensing canisters is used to store various types of skincare, cosmetic, food, and pharmaceutical products. Each of the plurality of plungers is used to dispense products from a corresponding dispensing canister. Each of the plurality of plungers is controlled by the dispensing actuation hub. The device includes a microprocessor housed within the tubular housing and used to control which products are dispensed by the dispensing actuation hub. The device is powered by power supply which is also housed within the tubular housing. A mixing chamber is included within the tubular housing and provides a space for multiple products to be blended.

14 Claims, 11 Drawing Sheets

US 10,076,175 B2

DEVICE FOR STORING, MIXING, AND APPLYING COSMETIC, SKINCARE, FOOD, OR PHARMACEUTICAL PRODUCTS

The current application claims a priority to the U.S. Provisional Patent application Ser. No. 62/135,295 filed on Mar. 19, 2015. The current application is filed on Mar. 21, 2016 while Mar. 19, 2016 was on a weekend.

FIELD OF THE INVENTION

The present invention generally relates to electronic dispensers of cosmetics and skincare products. More specifically, the present invention relates to a programmable device that is capable of dispensing specific amounts of cosmetic, skincare, food, or pharmaceutical products which may be blended together to create unique color, texture, or compositional mixtures.

BACKGROUND OF THE INVENTION

Cosmetic and skincare products are widely used today but are often packaged in separate containers. Different types of cosmetics or skincare products, such as lipstick, nail polish, sun screen, and lotions are generally separated because they are used on different parts of the body and have compositions which are not intended to be mixed. Moreover, different colors of lipstick, nail polish, etc. are also contained separately and only have a single color to offer. For people who use multiple products, organization can be a hassle. Furthermore, keeping a large number of products readily available when on-the-go can be difficult.

Accordingly, there is a present need for a device that can be used to store and dispense custom blended products as needed by the user. The present invention is a device for mixing and applying cosmetic, skincare, food, or pharmaceutical products which uses multiple dispensing canisters to separate different products hygienically. Based on the needs of the user, the present invention may be programmed by a compatible computer, smartphone, or electronic device to dispense a single product or a mixture of multiple products contained inside the canisters. In doing this, various color combinations and custom formulations can be achieved. Moreover, different types of products may be mixed if applicable. For example, sun screen and moisturizers may be mixed to provide protection from ultraviolet rays and prevent dry skin. Because all of the products are stored inside the device, the present invention eliminates clutter and improves portability.

DETAILED DESCRIPTION OF THE INVENTION

All illustrations of the drawings are for the purpose of describing selected versions of the present invention and are not intended to limit the scope of the present invention.

Figure 1:
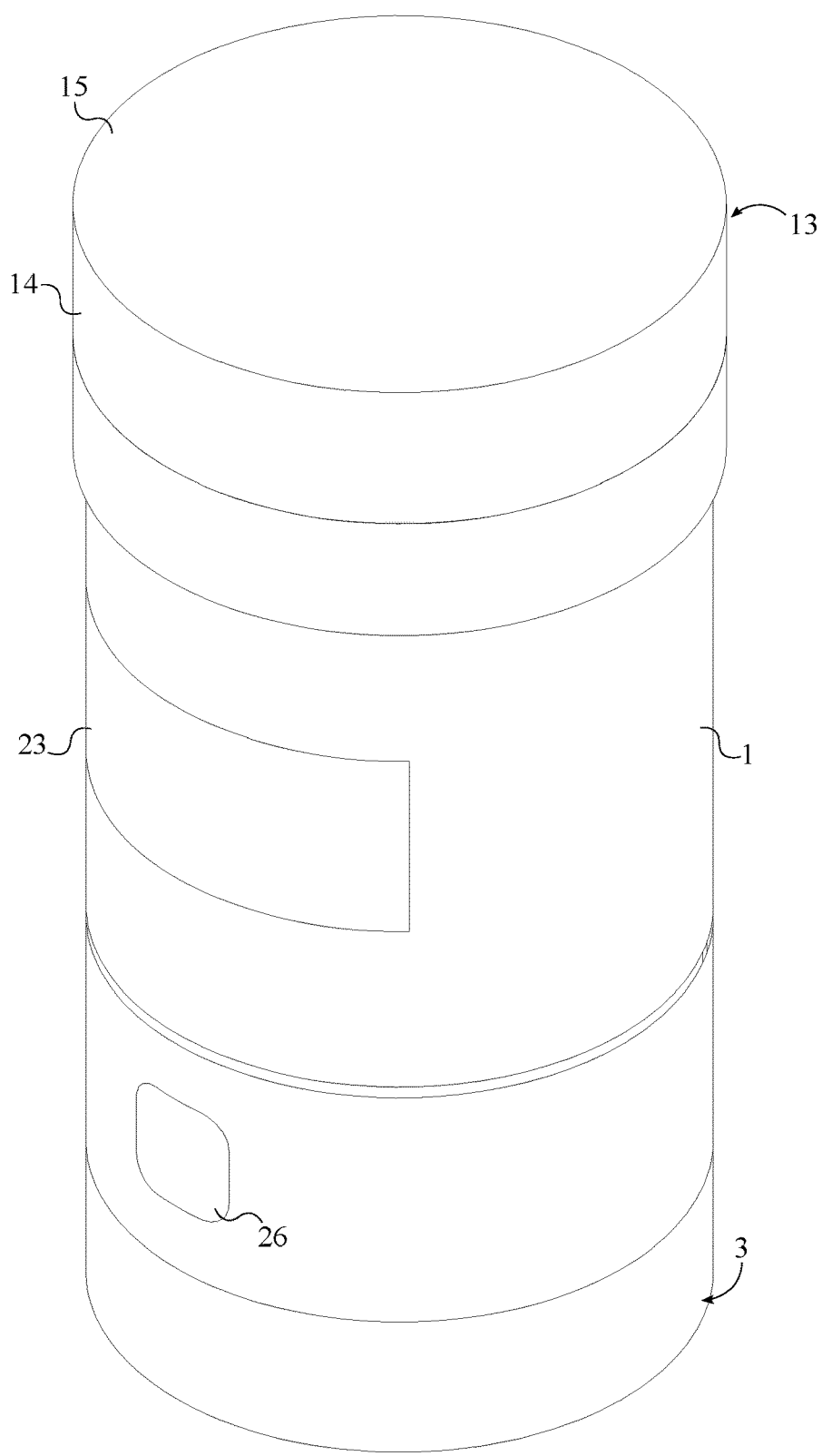
FIG. 1 is a front perspective view of the present invention.
Figure 3:
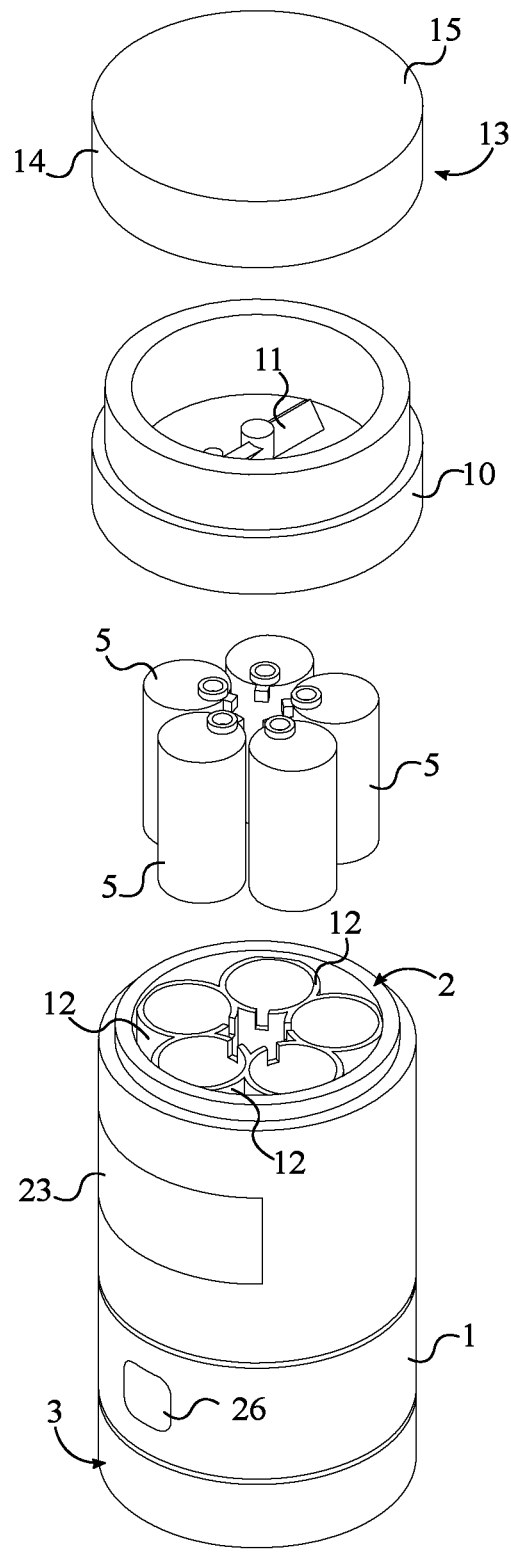
FIG. 3 is an exploded front perspective view of the present invention.
Figure 4:
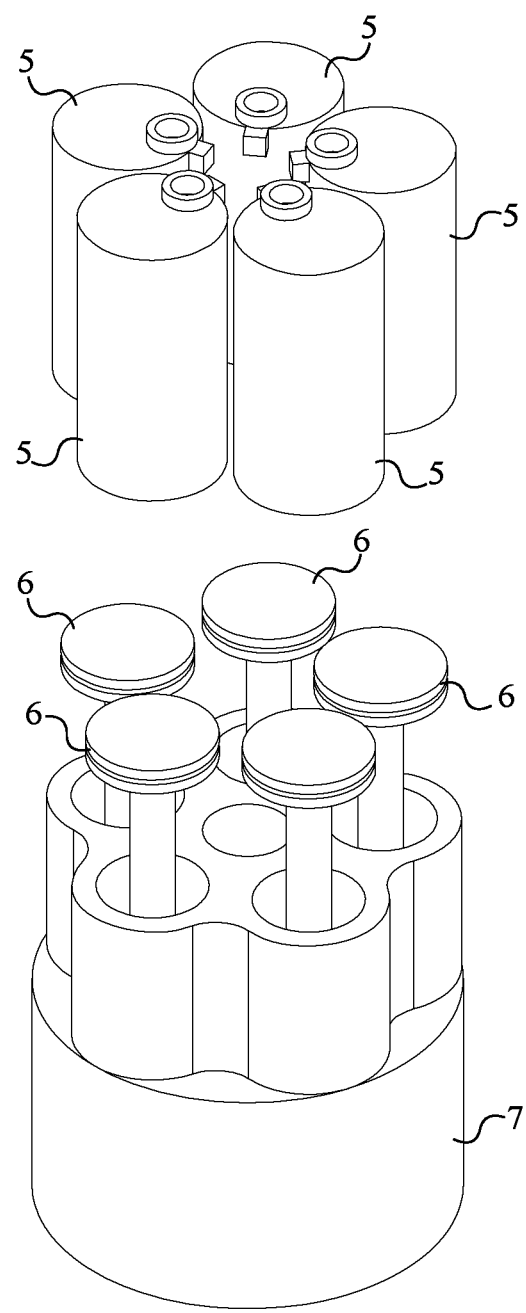
FIG. 4 is an exploded front perspective view of the dispensing actuation hub and the plurality of dispensing canisters.
Figure 7:
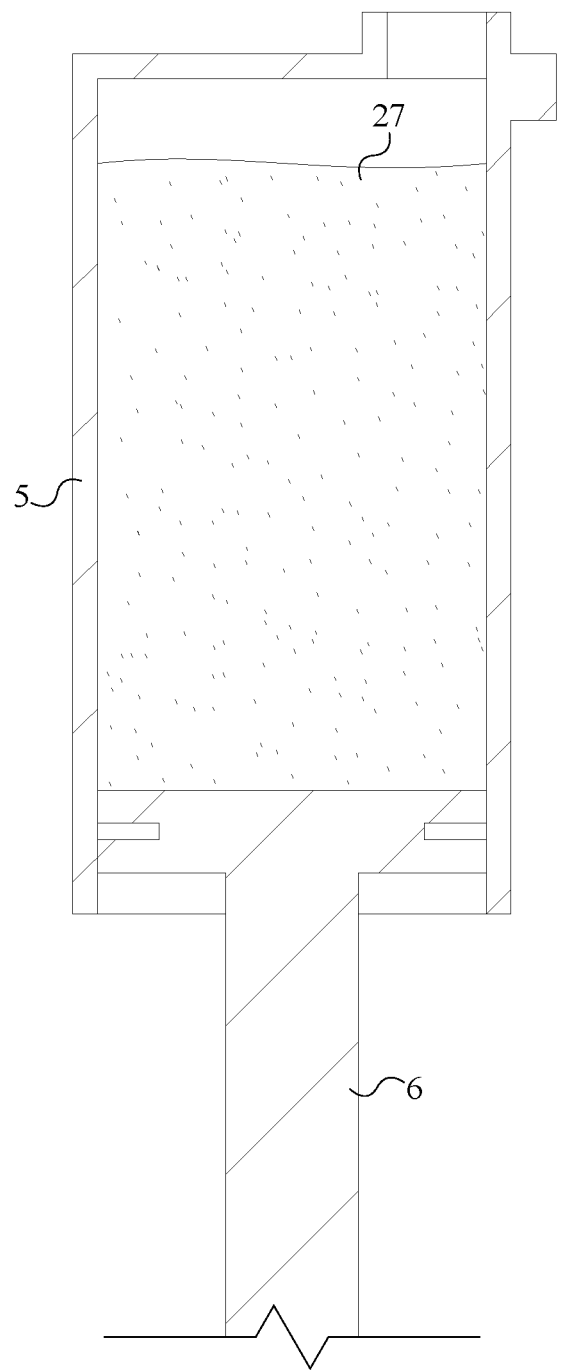
FIG. 7 is a cross-sectional schematic view of a dispensing canister and a plunger.
Figure 11:
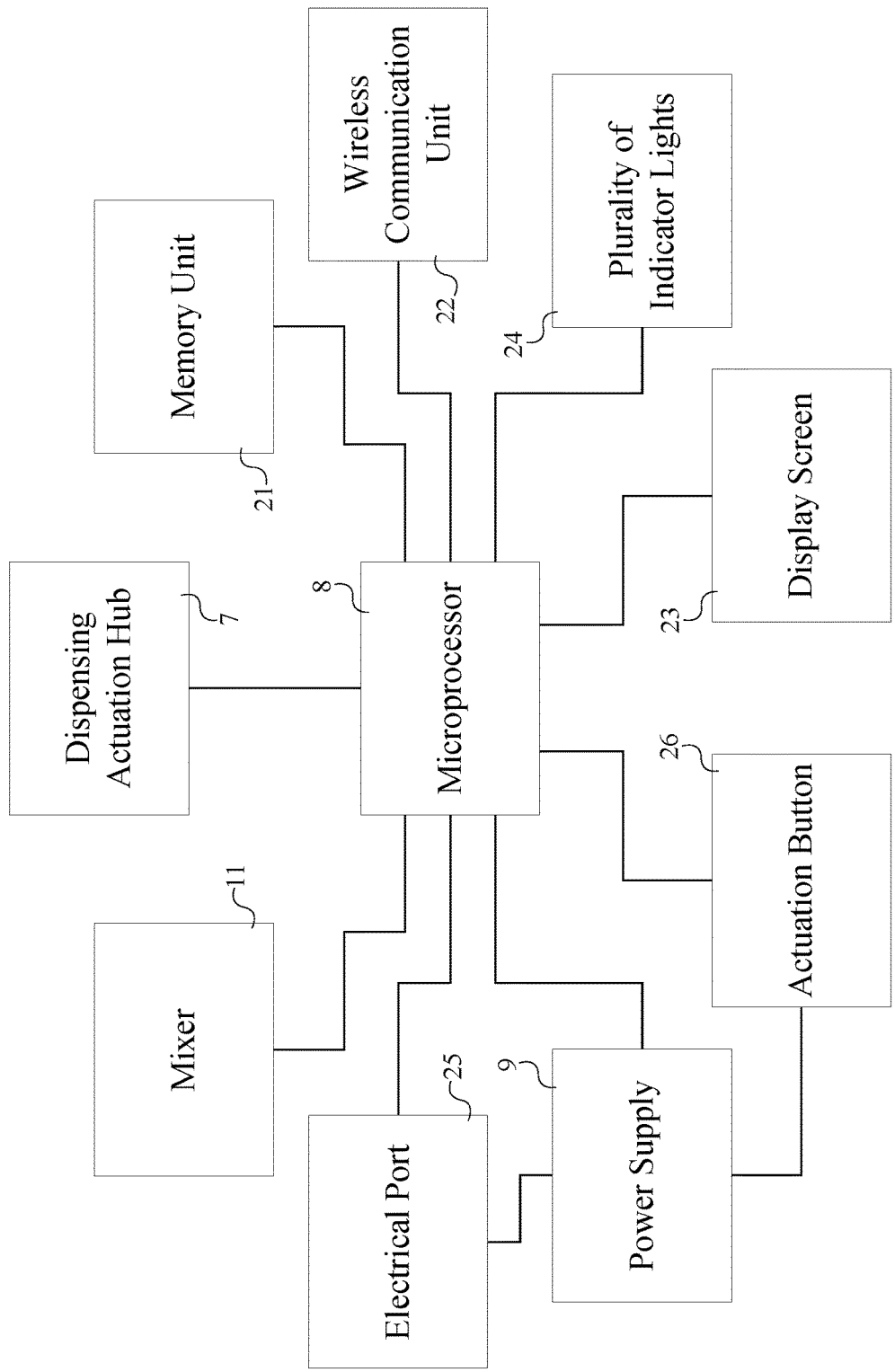
FIG. 11 is a schematic diagram showing the electrical and electronic connections of the present invention.

With reference to FIG. 1, FIG. 3, and FIG. 11, the present invention is a device for mixing and applying cosmetic, skincare, food, and pharmaceutical products. The present invention comprises a tubular housing 1, a plurality of dispensing canisters 5, a plurality of plungers 6, a dispensing actuation hub 7, a microprocessor 8, and a power supply 9. The tubular housing 1 is used to enclose the electrical components of the present invention and is held by the user while mixing and applying cosmetic or other products. The tubular housing 1 comprises an open end 2 and a closed end 3. The plurality of dispensing canisters 5 is attached within the tubular housing 1, adjacent to the open end 2. In the preferred embodiment of the present invention, a quantity of liquid-based product 27 is positioned within each of the plurality of dispensing canisters 5. This is shown in FIG. 7. The quantity of liquid-based product 27 may be individually dispensed based on the needs of the user and can be used for cosmetic, skincare, or pharmaceutical purposes. Alternatively, the liquid-based product 27 may be a source of food. Each of the plurality of plungers 6 is operatively integrated into a corresponding canister from the plurality of dispensing canisters 5 and is used to dispense the contents of the corresponding canister. Each of the plurality of plungers 6 is operatively coupled to the dispensing actuation hub 7 which is used to separately move each of the plurality of plungers 6. The dispensing actuation hub 7 is mounted within the tubular housing 1, adjacent to the closed end 3. This allows the dispensing actuation hub 7 to push one or more of the plurality of plungers 6 towards the plurality of dispensing canisters 5 in order to dispense one or more products.

In reference to FIG. 11, the microprocessor 8 and the power supply 9 are mounted within the tubular housing 1. The microprocessor 8 is electronically connected to the dispensing actuation hub 7 and is used to control the dispensing actuation hub 7. Further, the microprocessor 8 is used to manage the proportions of products dispensed if the user requires a mixture of two or more products. In the preferred embodiment of the present invention, the microprocessor 8 is mounted onto a printed circuit board (PCB) which is positioned adjacent to the dispensing actuation hub 7, opposite to the plurality of plungers 6. The power supply 9 is electrically connected to the microprocessor 8, which allows the microprocessor 8 to distribute power from the power supply to the other electronic components of the present invention. Consequently, the power supply 9 is used to power the microprocessor 8 and the dispensing actuation hub 7. In the preferred embodiment of the present invention, the power supply 9 is a rechargeable battery; however non-rechargeable batteries may alternatively be used. In the preferred embodiment, the power supply 9 is positioned in between the PCB and the closed end 3.

When the user wishes to dispense a product or mixture of products, the microprocessor 8 must have first received a product selection. The product selection may be made through a mobile application or some similar program which displays product information. In the event that the product selection corresponds with a mixture of two or more products, the product selection comprises a selection composition which details the necessary ratios of products needed to satisfy a specific product selection.

Figure 5:
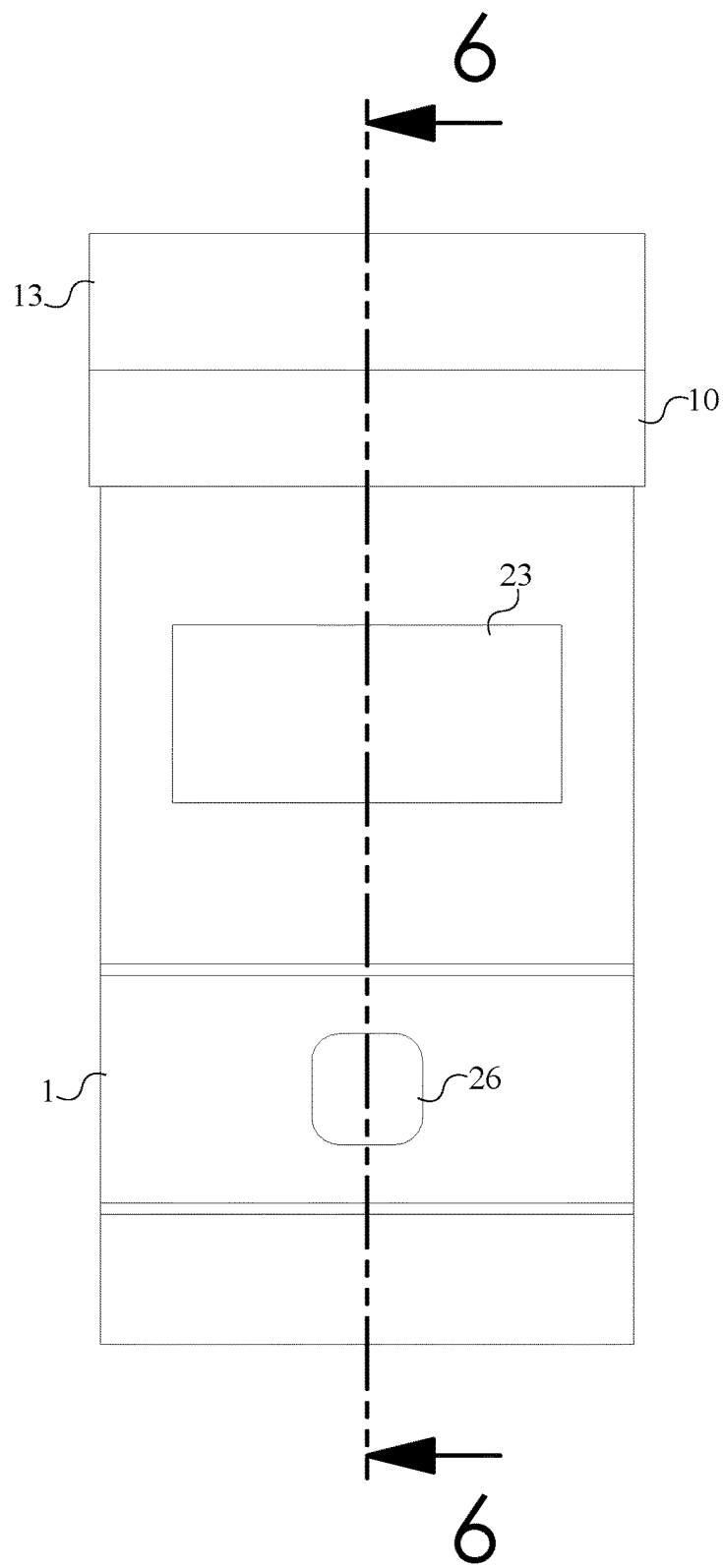
FIG. 5 is a front view of the present invention.
Figure 6:
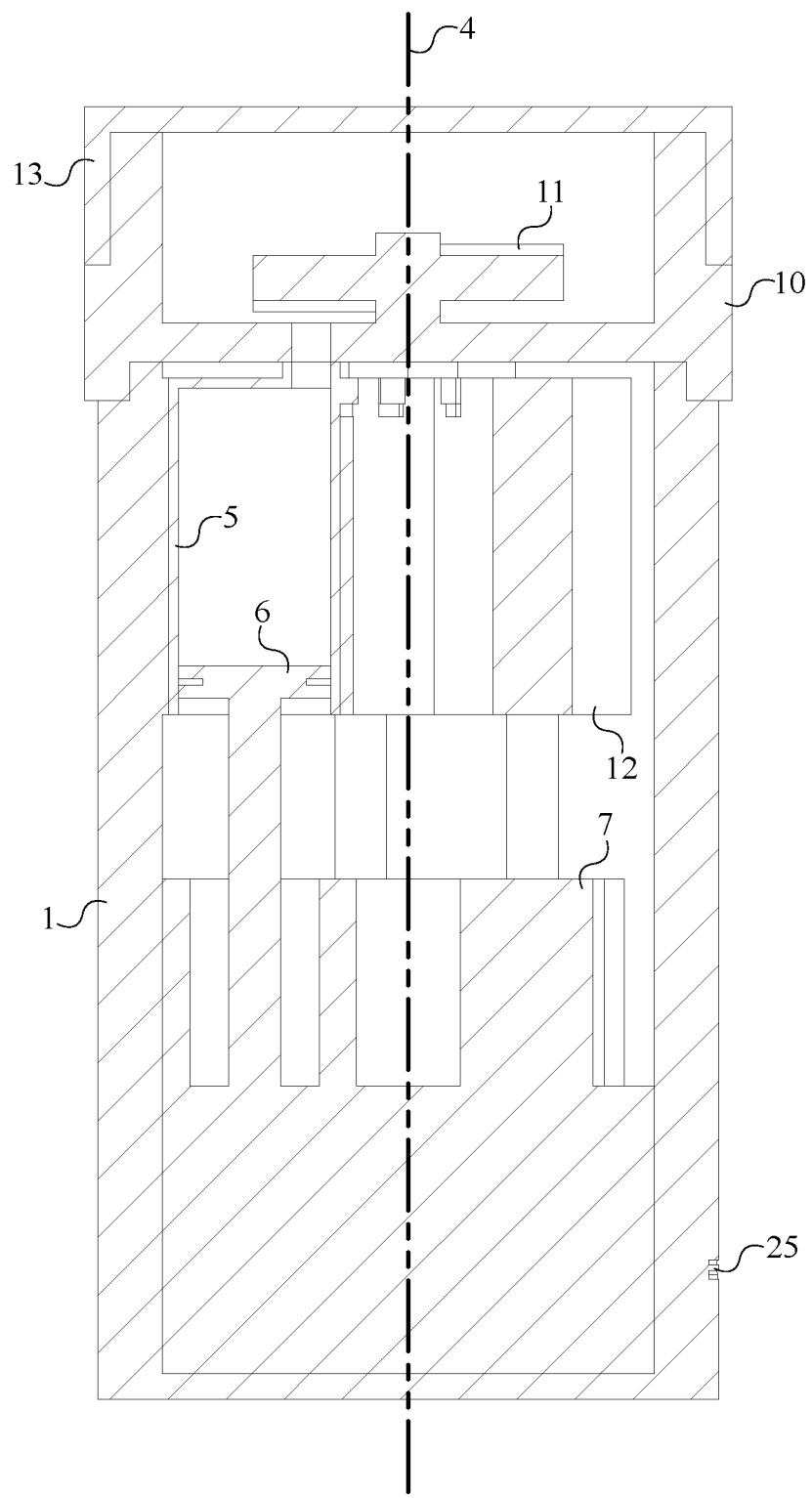
FIG. 6 is a section view of the present invention taken about the line 6 in FIG. 5.

In reference to FIGS. 5-6, the present invention further comprises a mixing chamber 10. The mixing chamber 10 is mounted into the open end 2 and provides a space for products to be held such that two or more products may be mixed together. Further, the mixing chamber 10 may be removed from the tubular housing 1, creating a mobile container for the user to carry mixed products. Removing the mixing chamber 10 also allows the user to interchange or replace each of the plurality of dispensing canisters 5 as needed. Each of the plurality of dispensing canisters 5 is in fluid communication with the mixing chamber 10 so that products may be dispensed directly into the mixing chamber 10.

In the preferred embodiment of the present invention, a mixer 11 is used to automatically blend products dispensed from the plurality of dispensing canisters 5. In reference to FIG. 6, the mixer 11 is mounted within the mixing chamber 10 and is electronically connected to the microprocessor 8. This configuration allows the microprocessor 8 to trigger the use of the mixer 11 once products are dispensed into the mixing chamber 10. In an alternative embodiment of the present invention, a mixer 11 is not included, requiring that the user blend products manually.

In reference to FIG. 3, the present invention further comprises a plurality of canister collars 12 which is used to secure the plurality of dispensing canisters 5 in place within the tubular housing 1. The plurality of canister collars 12 is laterally connected within the tubular housing 1 and is radially distributed about a central axis 4 of the tubular housing 1. To secure the plurality of dispensing canisters 5 within the tubular housing 1, each of the plurality of dispensing canisters 5 is mounted into a corresponding collar from the plurality of canister collars 12. This arrangement allows for individual dispensing canisters 5 to be replaced or interchanged as needed.

In reference to FIG. 3, the present invention further comprises a cap 13 which is used to cover the open end 2 of the tubular housing 1. The cap 13 comprises a rim 14 and a base 15. The rim 14 is perimetrically and perpendicularly connected to the base 15 and is attached about the tubular housing 1. To do so, the rim 14 may engage with the tubular housing 1 by snapping or screwing onto the tubular housing 1. The base 15 is positioned adjacent to the open end 2 in order to prevent products from spilling out of the tubular housing 1. In a first embodiment of the cap 13, the cap 13 reflects the above description and is only used to prevent spills; however, in alternative embodiments, the cap 13 has added features.

Figure 8:
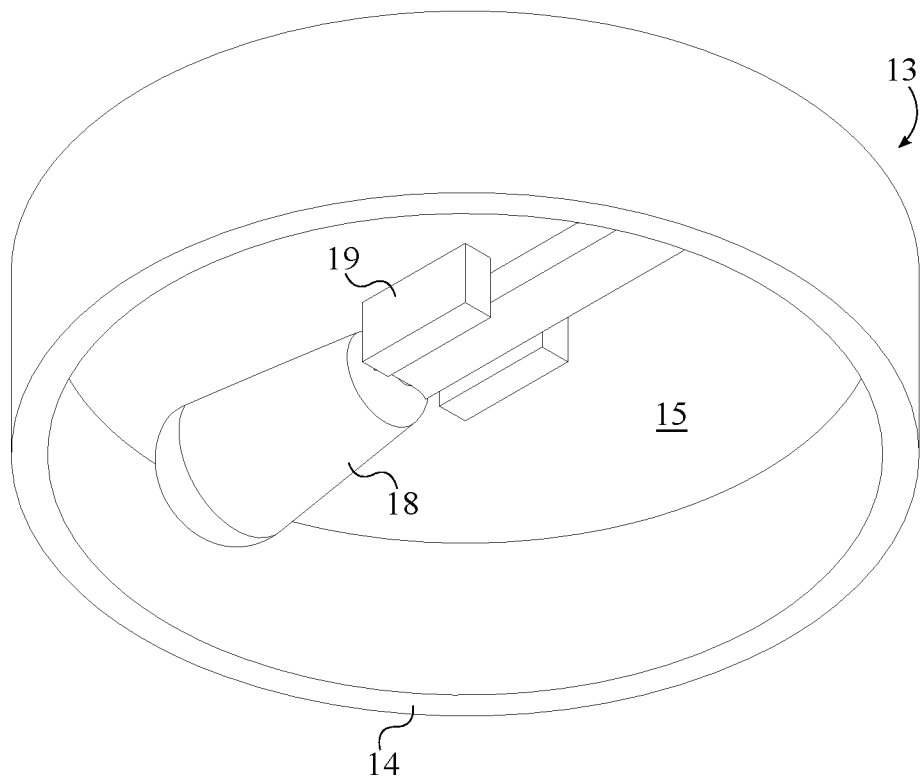
FIG. 8 is a bottom perspective view of the second embodiment of the cap, wherein the present invention comprises an applicator stick and an applicator clip.

In a second embodiment of the cap 13, the present invention further comprises an applicator stick 18 and an applicator clip 19. In reference to FIG. 8, the applicator clip 19 is connected adjacent to the base 15 and is encircled by the rim 14. The applicator clip 19 is used to attach and conceal the applicator stick 18 under the base 15. The applicator stick 18 is attached to the base 15 by the applicator clip 19 and is used to manually apply or mix products from the mixing chamber 10. The applicator stick 18 may have various applicator heads, including, but not limited to, foam heads, sponge heads, and brush heads.

Figure 9:
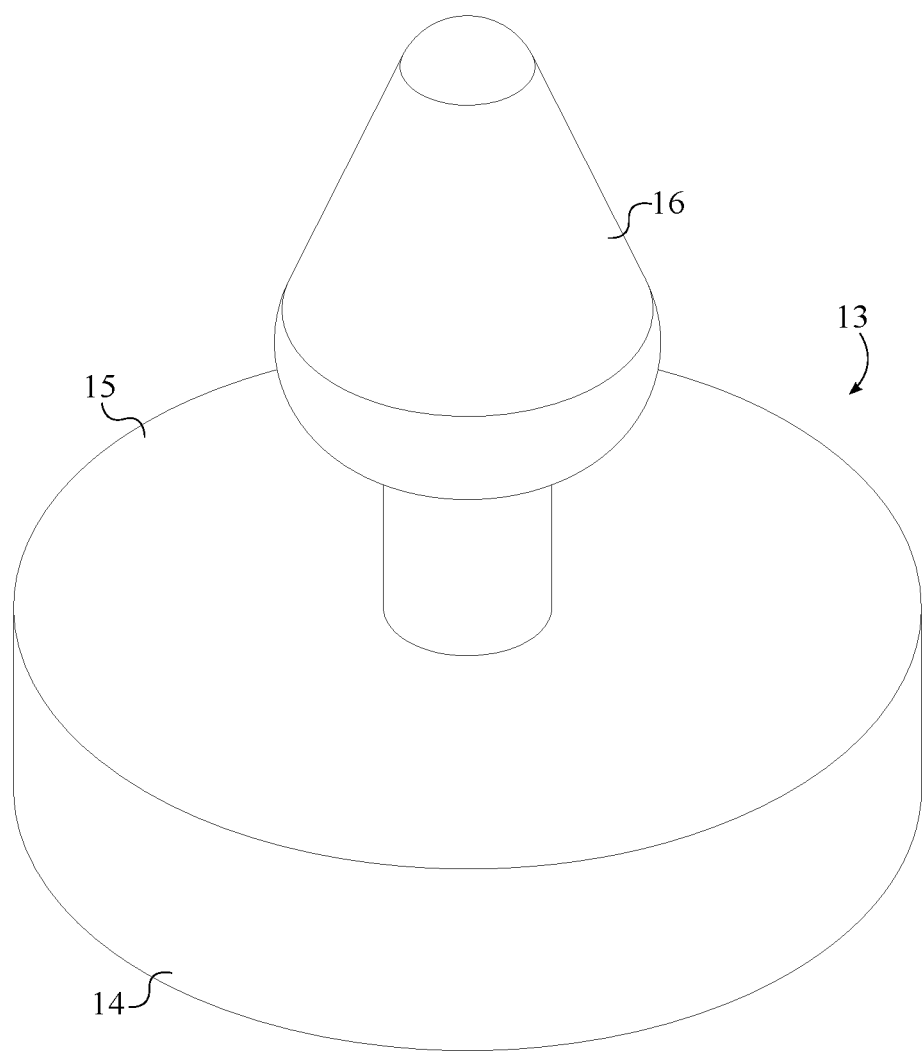
FIG. 9 is a perspective view of the third embodiment of the cap, wherein the cap comprises an applicator tip.

In a third embodiment of the cap 13, instead of the applicator clip 19 and the applicator stick 18, the cap 13 further comprises an applicator tip 16. In reference to FIG. 9, the applicator tip 16 is connected adjacent to the base 15, opposite to the rim 14. The applicator tip 16 is used to mix and apply products from the mixing chamber 10 after the products have been dispensed. The applicator tip 16 is positioned central and normal to the base 15. As a result, the applicator tip 16 acts as an extension of the tubular body which can be used to apply the liquid-based product 27 Similar to the applicator stick 18, the applicator tip 16 may have a foam head, a sponge head, or a brush head.

Figure 10:
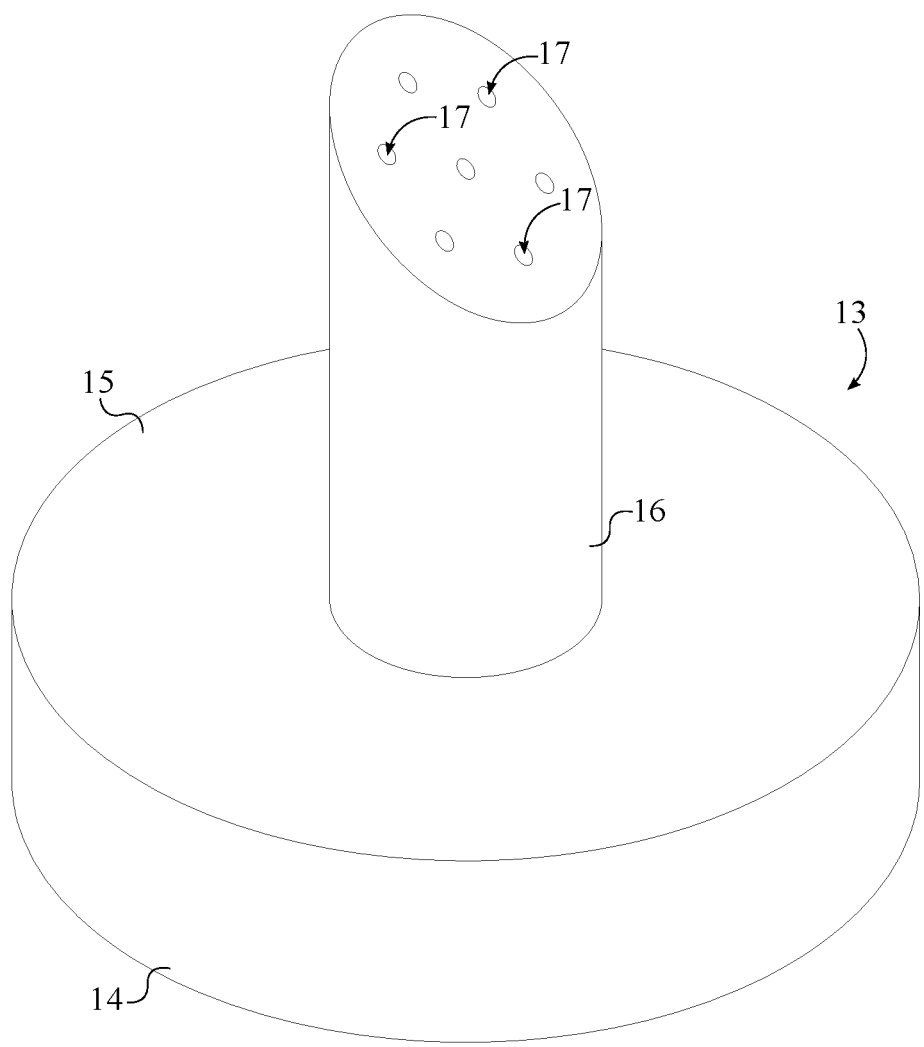
FIG. 10 is a perspective view of the fourth embodiment of the cap, wherein the cap comprises an applicator channel.

In a fourth embodiment of the cap 13, the applicator tip 16 is configured in the same manner as the third embodiment of the cap 13, wherein the applicator tip 16 is connected adjacent to the base 15, opposite to the rim 14, and is positioned central and normal to the base 15. In this embodiment, however, the cap 13 further comprises a plurality of applicator channels 17. In reference to FIG. 10, the each of the plurality of applicator channels 17 traverses through the applicator tip 16. The plurality of applicator channels 17 is in fluid communication with the plurality of dispensing canisters 5 so that products may be dispensed by the plungers 6 and the dispensing actuation hub 7, blended in the mixing chamber 10, and applied to the user's face or body.

In reference to FIG. 11, the present invention further comprises a memory unit 21. The memory unit 21 is mounted within the tubular housing 1 and is used to store information regarding smartphones, computers, and other devices which are can be paired to the present invention. Additionally, the memory unit 21 is used to store information regarding the contents of each of the plurality of dispensing canisters 5. Further, the memory unit 21 stores information regarding which products or combination of products is dispensed based on the product selection received by the present invention. The memory unit 21 is electronically connected to the microprocessor 8 so that the microprocessor 8 may be used to store or overwrite information on the memory unit 21.

In reference to FIG. 11, the present invention further comprises a wireless communication unit 22. The wireless communication unit 22 is mounted within the tubular housing 1 and is used to wirelessly transfer information between the present invention and an external computing device such as a smartphone or computer. The wireless communication unit 22 is electronically connected to the microprocessor 8 so that information received by the present invention may be processed and stored in the memory unit 21. Further, the microprocessor 8 is used to determine which devices the wireless communication unit 22 may connect with. In the preferred embodiment of the present invention, the wireless communication unit 22 and the memory unit 21 are both mounted on the same PCB upon which the microprocessor 8 is mounted. This configuration allows the microprocessor 8, the memory unit 21, and the wireless communication unit 22 to be compactly fit into the tubular housing 1.

In reference to FIG. 1 and FIG. 11, the present invention further comprises a display screen 23. The display screen 23 is laterally integrated into the tubular housing 1 and is used to show information pertaining to the various functions of the present invention. Such information can include, but is not limited to: the remaining battery life of the power supply 9, the currently selected product or mixture, and the amount of product available in each of the dispensing canisters 5. The display screen 23 is electronically connected to the microprocessor 8 so that the microprocessor 8 may be used to control what information is displayed.

Figure 2:
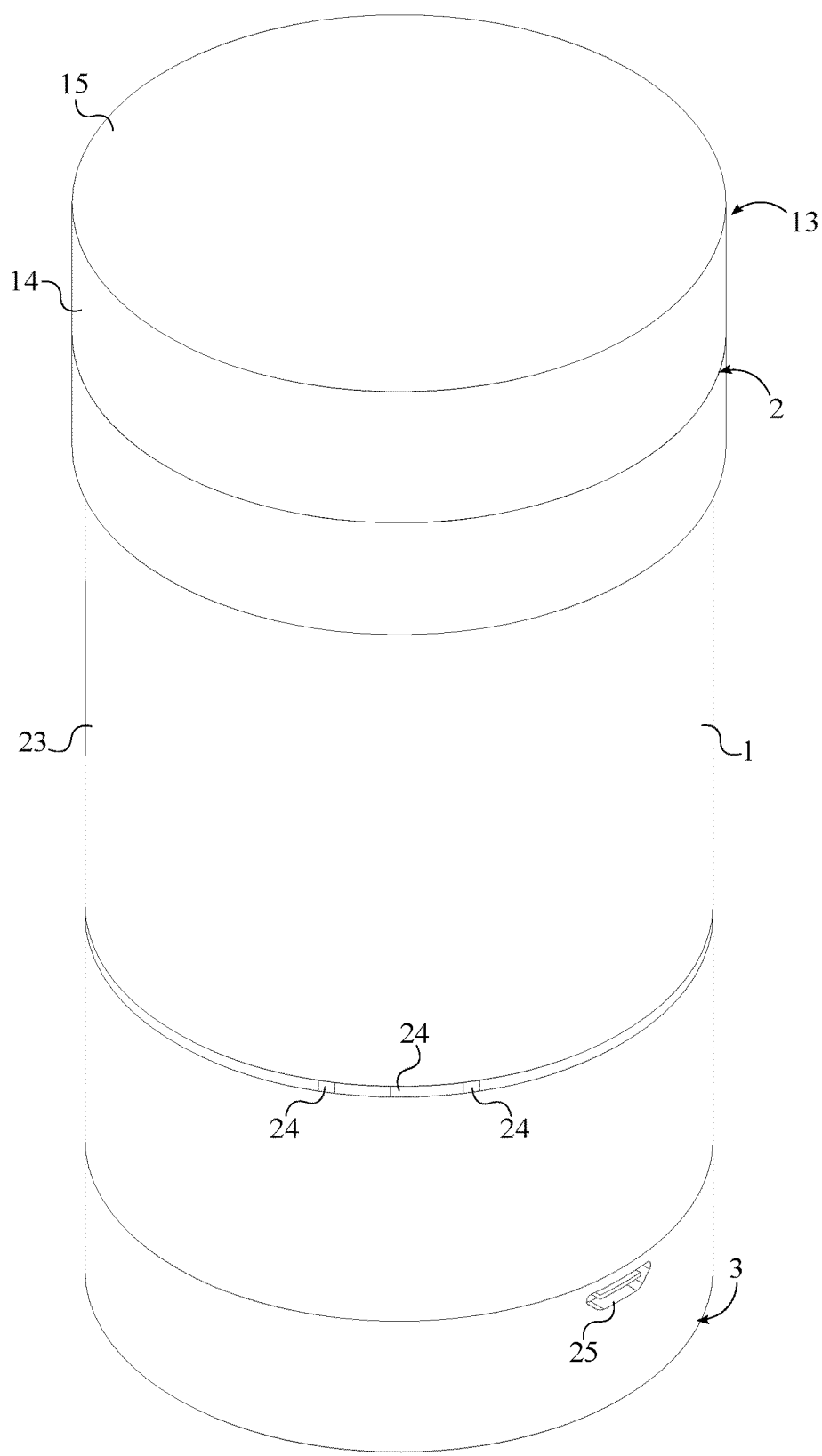
FIG. 2 is a rear perspective view of the present invention.

In reference to FIG. 2 and FIG. 11, the present invention further comprises a plurality of indicator lights 24. The plurality of indicator lights 24 is laterally mounted into the tubular housing 1 and may be used in addition to, or instead of, the display screen 23 to relay information to the user. Like the display screen 23, the plurality of indicator lights 24 is electronically connected to the microprocessor 8 so that the microprocessor 8 may be used to control what information is displayed to the user.

In reference to FIG. 2 and FIG. 11, the present invention further comprises an electrical port 25 which can be used to recharge the power supply 9 or transfer information between the present invention and an external computing device. The electrical port 25 is laterally mounted into the tubular housing 1. In order to recharge the power supply 9, the electrical port 25 is electrically connected to the power supply 9. Similarly, in order to transfer information between the present invention and an external computing device, the electrical port 25 is electronically connected to the microprocessor 8. This is useful if the user does not have a device which is capable of wirelessly communicating with the present invention.

In reference to FIG. 1 and FIG. 11, the present invention further comprises an actuation button 26 which is laterally integrated into the tubular housing 1. The actuation button 26 provides the user with a means of controlling how much of the liquid-based product 27 is dispensed. The actuation button 26 is electrically connected to the power supply 9. This allows the actuation button 26 to be used to turn the present invention on or off. The actuation button 26 is also electronically connected to the microprocessor 8, allowing the actuation button 26 to be used to control the dispensing and mixing of makeup and skincare products.

Although the invention has been explained in relation to its preferred embodiment, it is to be understood that many other possible modifications and variations can be made without departing from the spirit and scope of the invention as hereinafter claimed.

What is claimed is:

1. A device for storing, mixing and applying skincare, cosmetic, food, and pharmaceutical products comprising:
   a tubular housing;
   a plurality of dispensing canisters;
   a plurality of plungers;
   a dispensing actuation hub;
   a microprocessor;
   a power supply;
   a plurality of canister collars;
   the tubular housing comprising an open end and a closed end;
   the plurality of dispensing canisters being attached within the tubular housing, adjacent to the open end;
   each of the plurality of plungers being operatively integrated into a corresponding canister from the plurality of dispensing canisters, each of the plurality of plungers being used to dispense contents of the corresponding canister;
   each of the plurality of plungers being operatively coupled to the dispensing actuation hub, the dispensing actuation hub being used to separately move each of the plurality of plungers;
   the dispensing actuation hub being mounted within the tubular housing, adjacent to the closed end;
   the microprocessor and the power supply being mounted within the tubular housing;
   the microprocessor being electronically connected to the dispensing actuation hub;
   the power supply being electrically connected to the microprocessor;
   the plurality of canister collars being laterally connected within the tubular housing;
   the plurality of canister collars being radially distributed about a central axis of the tubular housing;
   each of the plurality of dispensing canisters being accommodated within a corresponding collar from the plurality of canister collars; and
   each of the plurality of plungers being inserted into a corresponding collar from the plurality of canister collars.

2. The device for storing, mixing and applying skincare, cosmetic, food, and pharmaceutical products as claimed in claim 1 comprising:
   a mixing chamber;
   the mixing chamber being mounted into the open end; and
   each of the plurality of dispensing canisters being in fluid communication with the mixing chamber.

3. The device for storing, mixing and applying skincare, cosmetic, food, and pharmaceutical products as claimed in claim 2 comprising:
   a mixer;
   the mixer being mounted within the mixing chamber; and
   the mixer being electronically connected to the microprocessor.

4. The device for storing, mixing and applying skincare, cosmetic, food, and pharmaceutical products as claimed in claim 1, wherein a quantity of liquid-based product is positioned within each of the plurality of dispensing canisters.

5. The device for storing, mixing and applying skincare, cosmetic, food, and pharmaceutical products as claimed in claim 1 comprising:
   a cap;
   the cap comprising a rim and a base;
   the rim being perimetrically and perpendicularly connected to the base;
   the rim being attached about the tubular housing; and
   the base being positioned adjacent to the open end.

6. The device for storing, mixing and applying skincare, cosmetic, food, and pharmaceutical products as claimed in claim 5 comprising:
   an applicator stick;
   an applicator clip;
   the applicator clip being connected adjacent to the base;
   the applicator clip being encircled by the rim; and
   the applicator stick being attached to the base by the applicator clip.

7. The device for storing, mixing and applying skincare, cosmetic, food, and pharmaceutical products as claimed in claim 5 comprising:
   the cap further comprising an applicator tip;
   the applicator tip being connected adjacent to the base, opposite to the rim; and
   the applicator tip being positioned central and normal to the base.

8. The device for storing, mixing and applying skincare, cosmetic, food, and pharmaceutical products as claimed in claim 5 comprising:
   the cap further comprising an applicator tip and a plurality of applicator channels;
   the applicator tip being connected adjacent to the base, opposite to the rim;
   the applicator tip being positioned central and normal to the base;
   each of the plurality of applicator channels traversing through the applicator tip and the base; and the plurality of applicator channels being in fluid communication with the plurality of dispensing canisters.

9. The device for storing, mixing and applying skincare, cosmetic, food, and pharmaceutical products as claimed in claim 1 comprising:
a memory unit;
the memory unit being mounted within the tubular housing; and
the memory unit being electronically connected to the microprocessor.

10. The device for storing, mixing and applying skincare, cosmetic, food, and pharmaceutical products as claimed in claim 1 comprising:
a wireless communication unit;
the wireless communication unit being mounted within the tubular housing; and
the wireless communication unit being electronically connected to the microprocessor.

11. The device for storing, mixing and applying skincare, cosmetic, food, and pharmaceutical products as claimed in claim 1 comprising:
a display screen;
the display screen being laterally integrated into the tubular housing; and
the display screen being electronically connected to the microprocessor.

12. The device for mixing and applying makeup as claimed in claim 1 comprising:
a plurality of indicator lights;
the plurality of indicator lights being laterally mounted into the tubular housing; and
the plurality of indicator lights being electronically connected to the microprocessor.

13. The device for storing, mixing and applying skincare, cosmetic, food, and pharmaceutical products as claimed in claim 1 comprising:
an electrical port;
the electrical port being laterally mounted into the tubular housing;
the electrical port being electrically connected to the power supply; and
the electrical port being electronically connected to the microprocessor.

14. The device for storing, mixing and applying skincare, cosmetic, food, and pharmaceutical products as claimed in claim 1 comprising:
an actuation button;
the actuation button being laterally integrated into the tubular housing;
the actuation button being electrically connected to the power supply; and
the actuation button being electronically connected to the microprocessor.

* * * * *